United States Patent [19]

Jacobson

[11] Patent Number: 4,545,374
[45] Date of Patent: Oct. 8, 1985

[54] METHOD AND INSTRUMENTS FOR PERFORMING A PERCUTANEOUS LUMBAR DISKECTOMY

[76] Inventor: Robert E. Jacobson, 1295 NW. 14th St., Suite G, Miami, Fla. 33125

[21] Appl. No.: 414,779

[22] Filed: Sep. 3, 1982

[51] Int. Cl.[4] .............................................. A61B 17/00
[52] U.S. Cl. ................................ 128/303 R; 128/305; 128/312; 128/348.1; 604/164; 604/264
[58] Field of Search .............. 128/348.1, 92 E, 92 EB, 128/303 R, 753-754, 341-343, 345, 3, 126, 305.3, 741, 303.11, 303.13, 783-784, 362; 604/22, 164-166, 264, 904

[56] References Cited

U.S. PATENT DOCUMENTS

| | | | |
|---|---|---|---|
| 2,991,787 | 7/1961 | Shelden et al. | 128/305.3 |
| 3,308,819 | 3/1967 | Arp | 604/164 |
| 3,320,131 | 5/1967 | Smith . | |
| 3,320,948 | 5/1967 | Martin | 128/17 |
| 3,384,087 | 5/1968 | Brummelkamp | 128/305.3 |
| 3,388,703 | 6/1968 | Bowes | 604/166 |
| 3,459,189 | 8/1969 | Alley et al. | 604/166 |
| 3,511,243 | 5/1970 | Toy | 128/305.3 |
| 3,530,860 | 9/1970 | Majoros . | |
| 3,606,878 | 9/1971 | Kellogg, Jr. . | |
| 3,612,050 | 10/1971 | Sheridan | 604/166 |
| 3,682,162 | 8/1972 | Colyer | 128/741 |
| 3,830,226 | 8/1974 | Stanb et al. | 128/741 |
| 3,844,274 | 10/1974 | Nordstrom . | |
| 3,870,048 | 3/1975 | Yoon . | |
| 3,913,584 | 10/1975 | Waichie . | |
| 3,964,480 | 6/1976 | Froning . | |
| 3,995,619 | 12/1976 | Glatzer . | |
| 4,043,343 | 8/1977 | Williams . | |
| 4,114,618 | 9/1978 | Vargas | 604/165 |
| 4,222,380 | 9/1980 | Terayama . | |
| 4,273,131 | 6/1981 | Olsen | 128/341 |
| 4,291,696 | 9/1981 | Ring | 604/904 |
| 4,369,768 | 1/1983 | Vukovic | 128/6 |
| 4,411,655 | 10/1983 | Schreck | 604/165 |

OTHER PUBLICATIONS

"Nucleography", May 1952, issue of Journal of Bone and Joint Surgery, vol. 34B, No. 2.
"Dr. Parvas Kanbin Develops New Surgical Procedure Aiding Herniated Spinal Disk Sufferers", May 1982, issue of Image, vol. 6, No. 5.
"Microlumbar Discectomy", Feb. 1982, issue of Resident and Staff Physician.
"Oh, My Aching Back", p. D1, Saturday, Nov. 7, 1981, issue of The Miami Herald.
"Percutaneous Lumbar Discectomy", 1981, Dr. Robert E. Jacobson.

Primary Examiner—C. Fred Rosenbaum
Assistant Examiner—Gene B. Kartchner
Attorney, Agent, or Firm—Pennie & Edmonds

[57] ABSTRACT

A method for percutaneously accessing the lumbar region of the spinal column by laterally inserting a cannula through the patient's side above the pelvic crest to contact a predetermined position in the lumbar region and passing objects such as medical instruments through the cannula. This method is useful for performing percutaneous lumbar diskectomies by cutting a portion of the patient's disc capsule and nucleus through the cannula and removing a desired amount of nucleus material. The cannula has a tubular member and anchor means attached to one end of the member for anchoring the cannula in body tissue to prevent shearing movement between it and the tissue. Other instruments for performing a percutaneous lumbar diskectomy are disclosed, including a speculum and trocar for percutaneously inserting the cannula into the patient's body, a diskectomy knife for cutting disc nucleus material and rongeur forceps for removing the disc material. The above instruments may be combined in a surgical apparatus.

32 Claims, 22 Drawing Figures

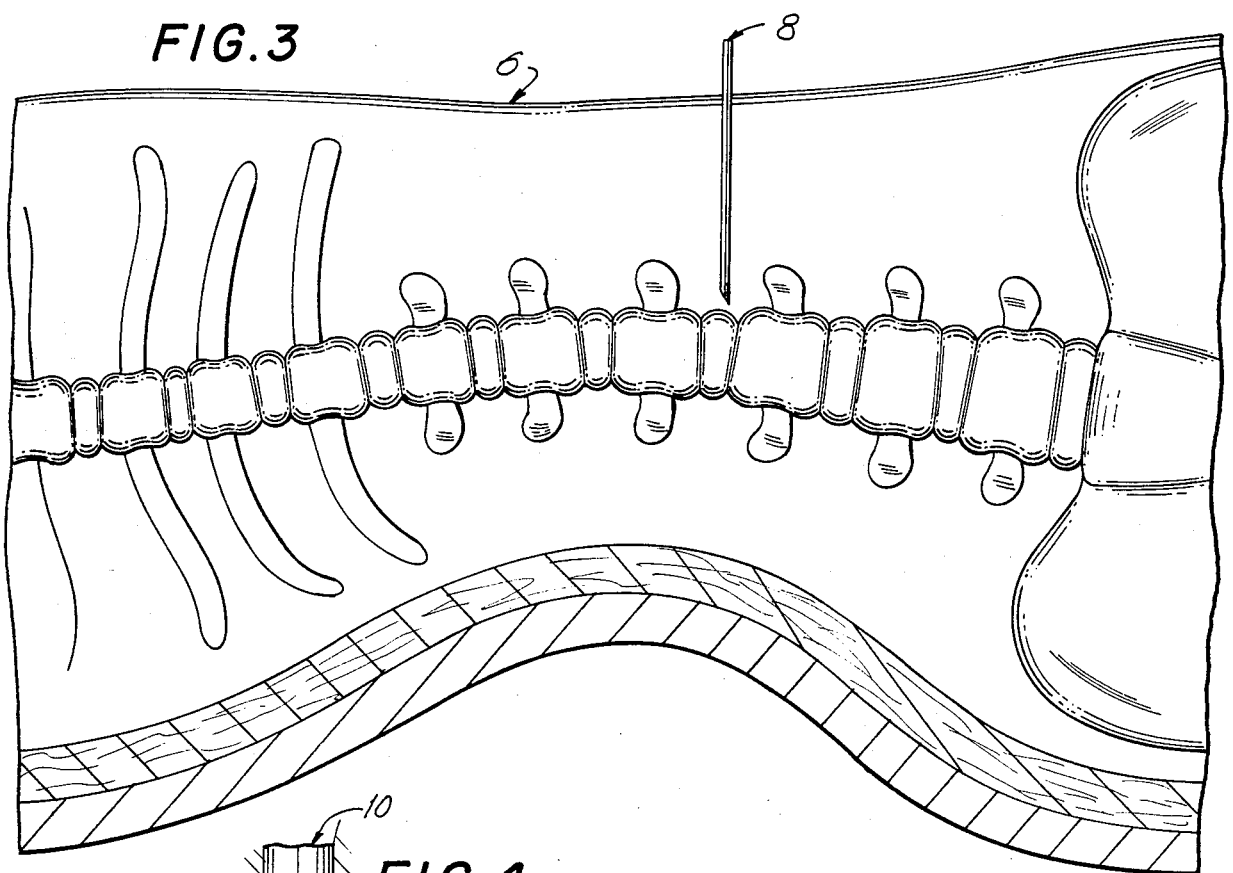
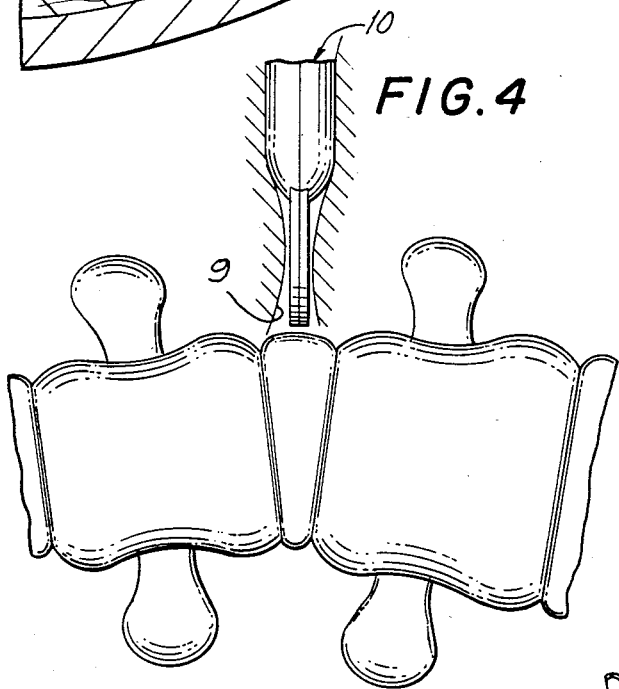
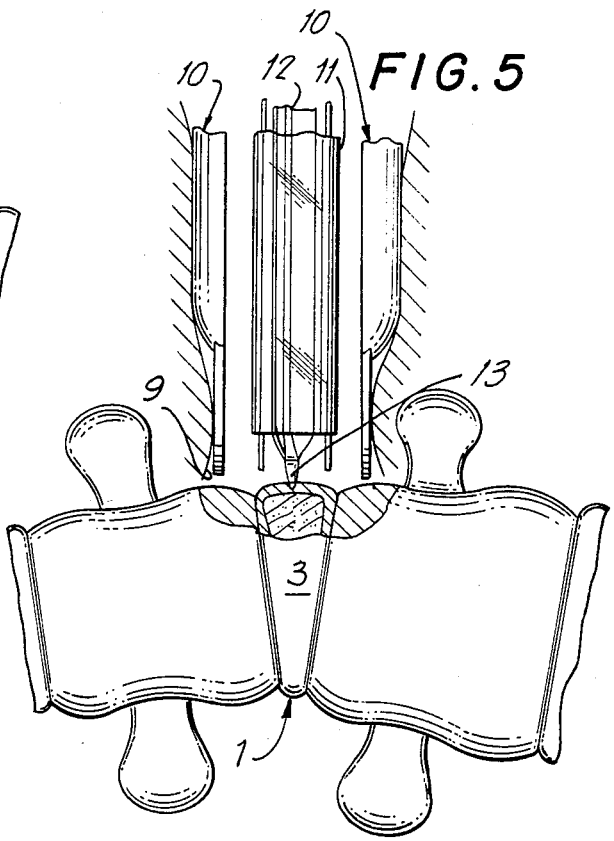

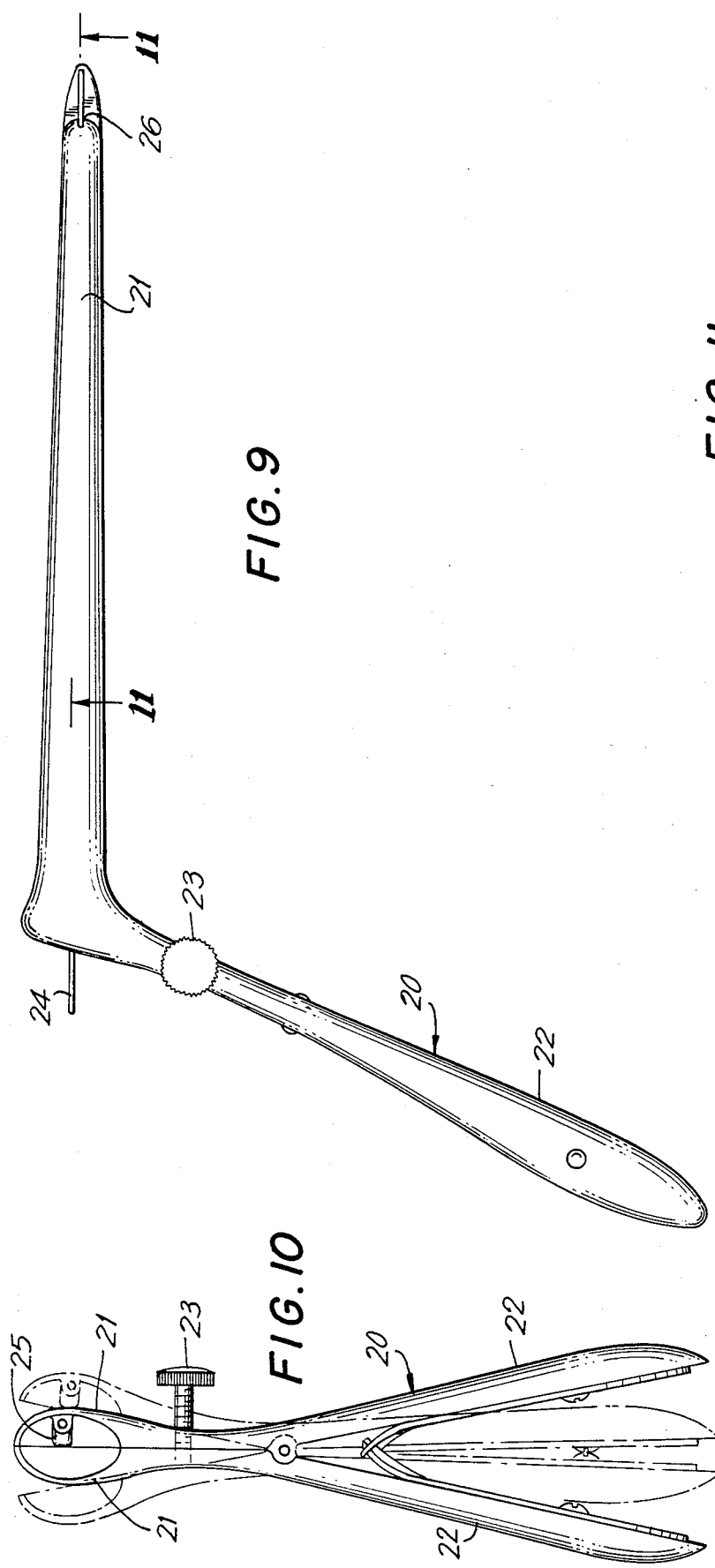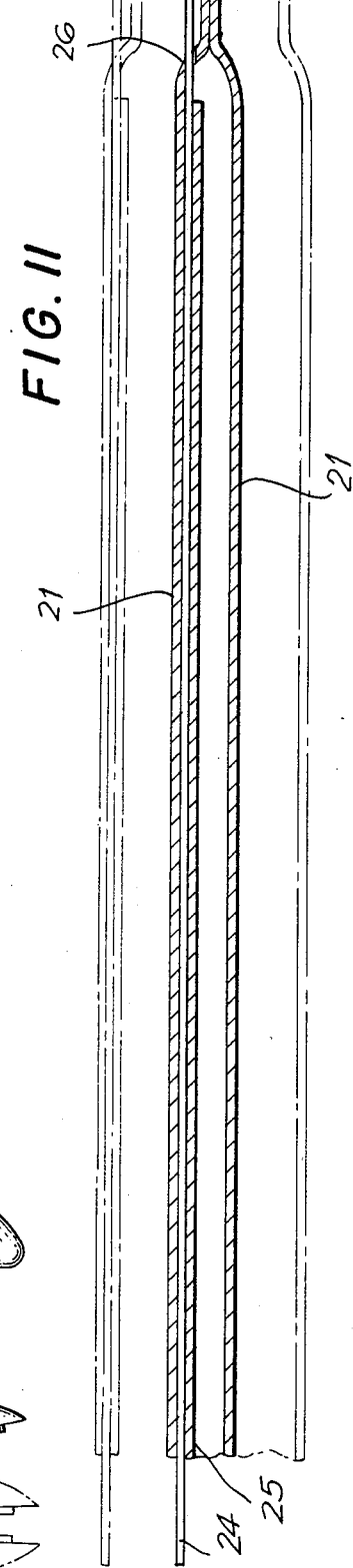

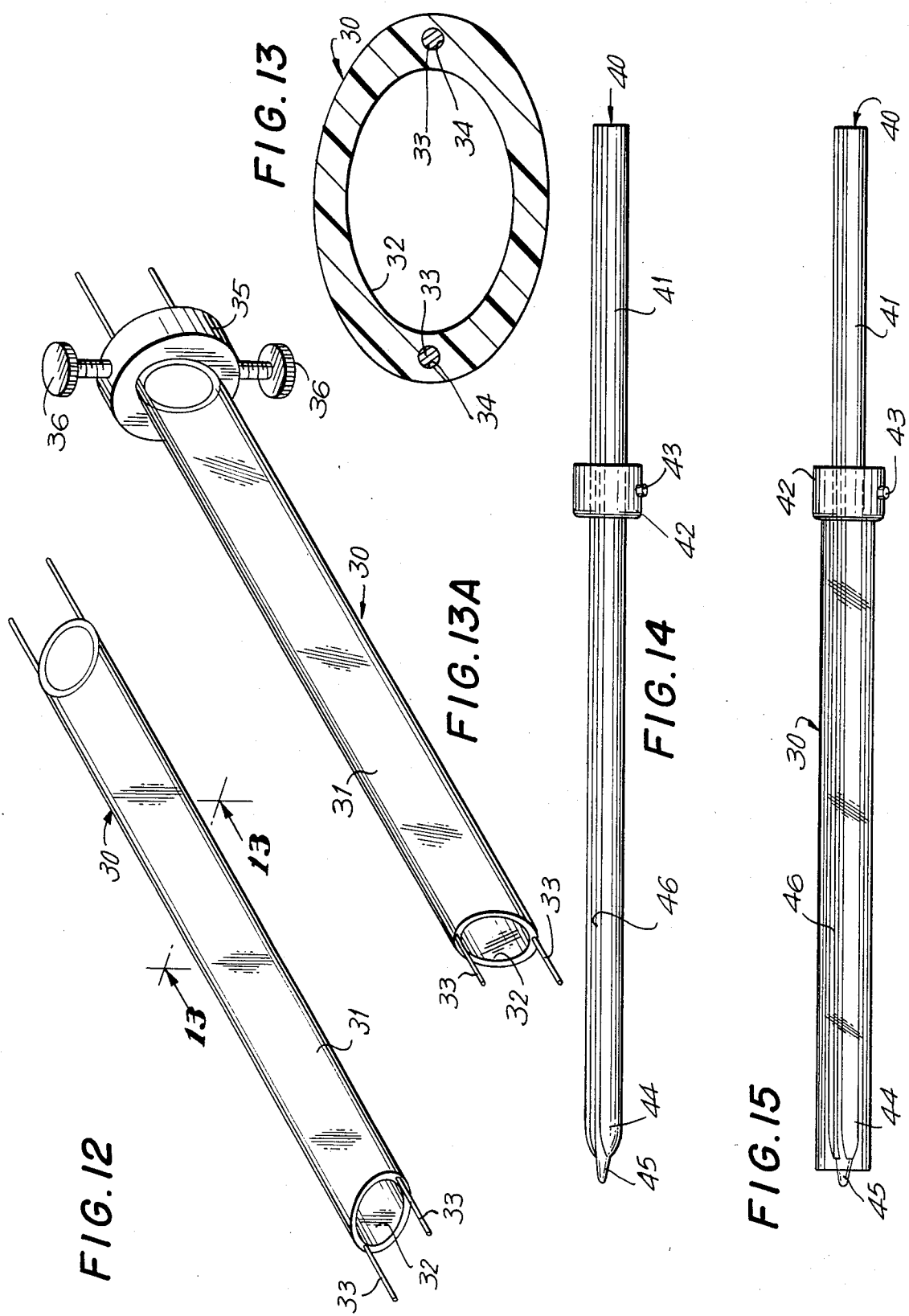

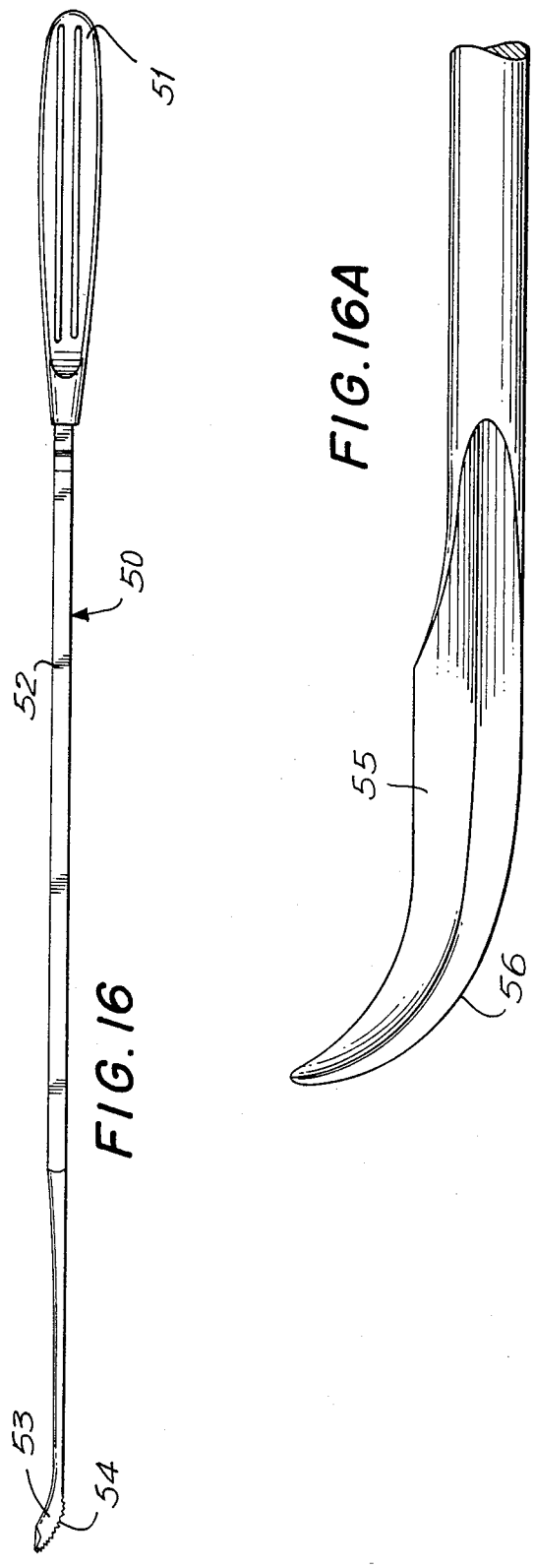
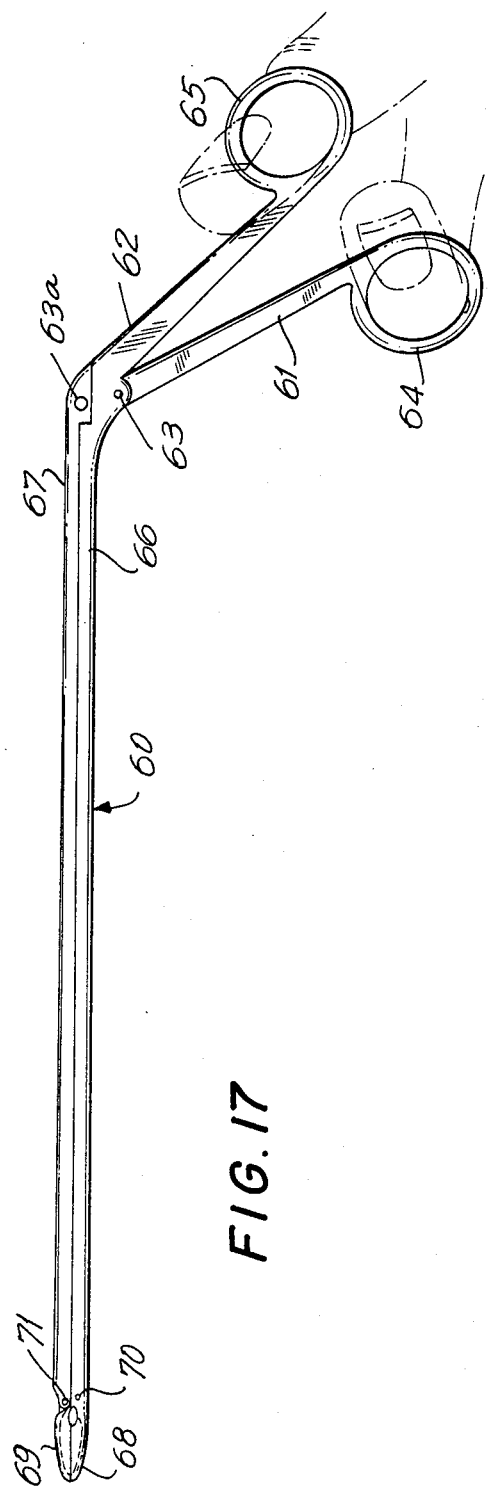

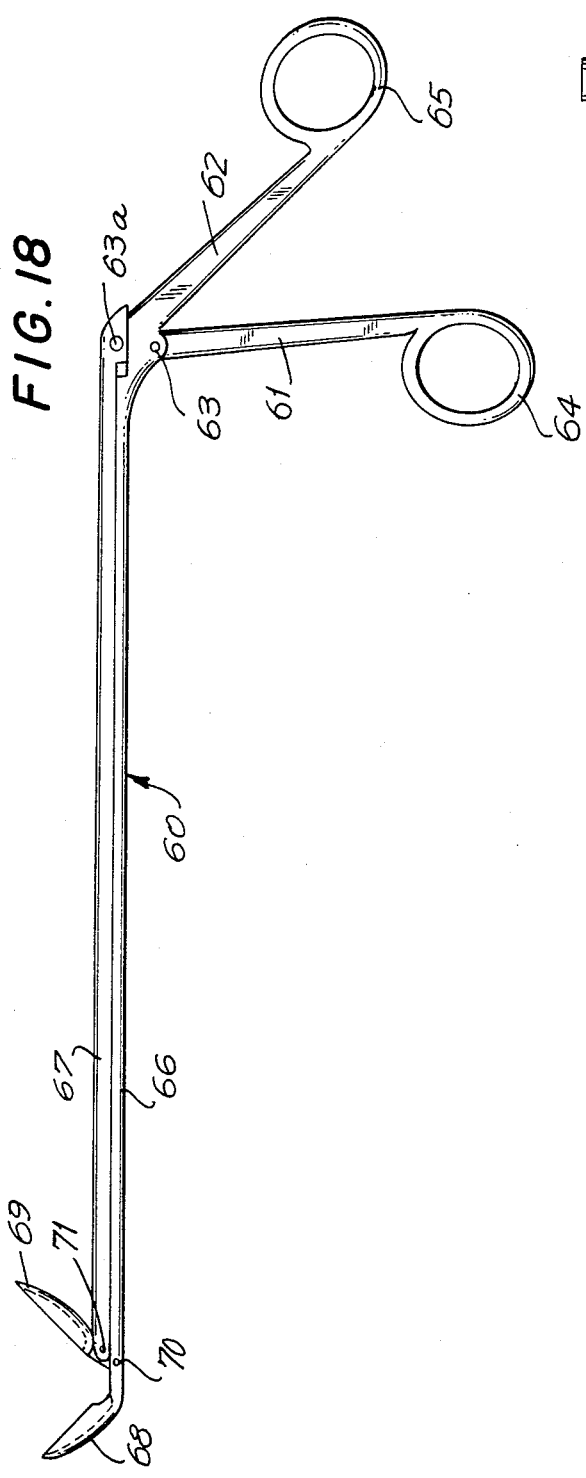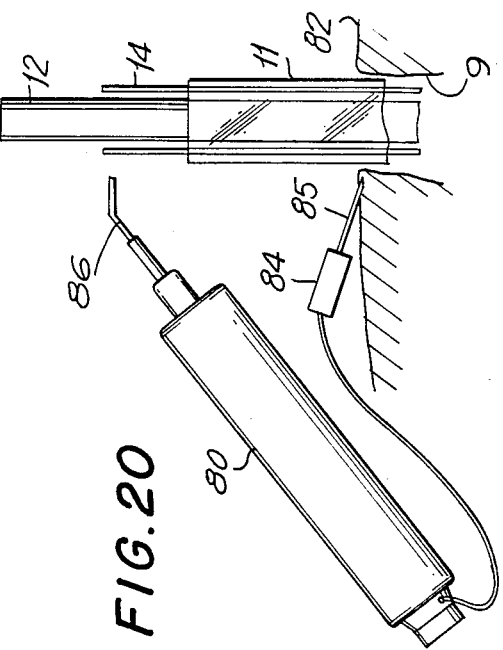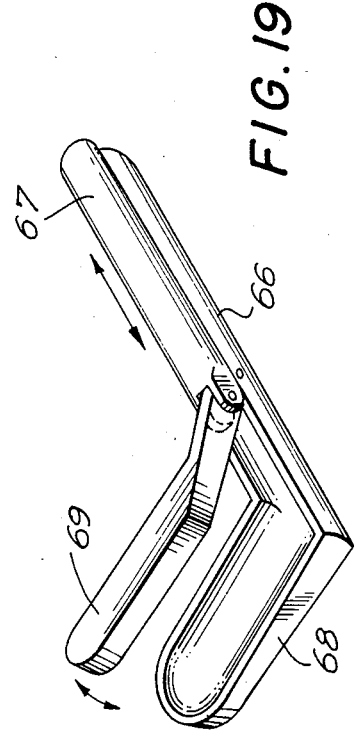

METHOD AND INSTRUMENTS FOR PERFORMING A PERCUTANEOUS LUMBAR DISKECTOMY

BACKGROUND OF THE INVENTION

1. Field of the Invention

The invention relates to a method and instruments to perform a percutaneous lumbar diskectomy.

2. Description of the Prior Art

Many people suffer from lower back pain in the lumbar region of their spines caused by a herniated or protruding lumbar vertebral disc which is often called a slipped disc. Spinal discs are shock absorbing cushions between spinal vertebrae. FIG. 1 shows a schematic view of a typical disc 1 sandwiched between two vertebrae 2. The disc has a fibrous capsule or annulus 3 which surrounds a cartilage-like nucleus 4 that has a consistency similar to a raw potato. Discs are avascular, that is, they have no blood vessels. In a herniated or bulging disc, there are small tears in the disc capsule which allow the nucleus material to bulge and expand around the tear. If the bulge contacts spinal nerves, the person may experience extreme shooting pain in his back or legs.

A slipped disc is treated by eliminating nerve contact. It has been found that bed rest and spinal traction may alleviate the pain in simple cases. In more serious cases, a portion of the affected disc nucleus has been surgically removed, which relieves the disc bulge, in a procedure known as a laminectomy.

Since the disc is confined within the spinal column, it must be accessed in order to remove nucleus material. In a laminectomy, nucleus access is obtained by cutting a channel from the rear of the patient's back through the vertebral lamina to the disc. A long incision of the order of six inches is made through the skin and fat layer to the lamina. The incision eventually heals as an unattractive scar. The surgeon cuts through the lamina and retracts body tissue including spinal nerves and blood vessels located around the dural sac 5 (a conduit for the nerves), ligaments and major back support muscles. Once the channel is cleared, the surgeon cuts a hole into the disc capsule through which he passes instruments in order to remove a portion of the disc nucleus. The procedure is normally performed in about one and one-half hours, while the patient is under general anesthesia.

In known laminectomy procedures, the surgeon does not visually inspect the nucleus removal because he is removing the material by feel. Since instruments are blindly inserted through the hole, very occasionally they overpenetrate through the other side of the disc and damage other tissue structure.

A laminectomy is a very destructive process. Cutting lamina and retracting spinal nerves, blood vessels, muscle and ligaments often leads to permanent scarring which may cause more permanent pain than the original slipped disc. Many people prefer to continue suffering pain caused by the herniated disc rather than risk permanent pain from the laminectomy. Laminectomies also require long hospitalization and hence postoperative recovery periods, typically from one to two months, if there have been no complications caused by the operation.

In the past, other procedures have been developed in order to alleviate disc herniation. One procedure was to inject a nucleus dissolving chymopapain enzyme into the disc with a spinal needle to relieve the pressure on the nerves. The United States Food and Drug Administration banned the use of chymopapain enzyme for this procedure in the mid-1970's. Clinical testing raised doubts concerning its effectiveness and its significant complications due to tissue reaction to the enzyme.

Another known procedure is a microsurgical diskectomy. As in a laminectomy, the disc is accessed by cutting a channel from the rear of the patient's back to the disc. However, by using a smaller incision and visual magnification with an operating microscope or operating loupes, small diameter microsurgical instruments can pass between the vertebral laminae without bone cutting and into the disc. Blood vessels and nerves are still retracted. Scarring and post operative pain is reduced, but not eliminated.

There has thus been a long felt need in the medical profession to reduce the cost, risk, pain, and recovery time of diskectomies. All of these drawbacks are materially reduced by performance of a percutaneous lumbar diskectomy disclosed herein.

SUMMARY OF THE INVENTION

The method according to the teaching of the present invention percutaneously accesses a the lumbar region of a patient's spinal column by laterally inserting a cannula through the patient's side above the pelvic crest to contact a predetermined position in the lumbar region and conducting a surgical procedure on the spinal column by manipulating instruments through the cannula. The lateral approach does not intersect bone, nerves, blood vessels, major back support muscles or ligaments which would otherwise have to be cut or retracted.

The above method is used to perform a percutaneous lumbar diskectomy procedure to access an injured spinal disc. The cannula is passed from just above the pelvic crest to a position where the cannula's open end contacts the injured disc. Then it is anchored to the disc. The cannula defines a percutaneous channel from outside the body to the disc. By passing specially designed instruments through the anchored cannula, the surgeon pierces the disc annulus and removes a portion of the nucleus in order to relieve disc bulging. Once the desired amount of nucleus is removed, the cannula is removed. The entire procedure is preferably monitored under fluoroscopic X-ray to insure proper cannula placement and manuvering of instruments therethrough.

A percutaneous lumbar diskectomy performed in accordance with the teachings of the present invention is not performed through the patient's back. There is no need to cut spinal laminae or to retract nerves, blood vessels, muscles or ligaments. Instruments constructed in accordance with the invention allow the procedure to be performed in approximately 15 minutes under only local anesthesia. By elimination of bone cutting and nerve retraction, the patient experiences no scar induced post-operative pain. Typically, the patient will completely convalesce within one to two days. Some patients are able to walk within hours after the procedure and may be released from the hospital on the same day.

Instruments constructed in accordance with the invention include a speculum, a trocar and a cannula, which create the percutaneous channel; a knife and rongeur forceps are passed down the cannula to remove the nucleus material.

The speculum is of the type having pivotally connected handles and semi-sharp blades; it is improved by having guide means on at least one of the blades for percutaneously guiding the speculum through body tissue on a guide member having a diameter of less than approximately 3 mm. The guide means maybe a bore defined by at least one blade and extending approximately parallel to the blade's longest dimension for slidable reception of the guide member. In use, the speculum slides along the guide member and creates a percutaneous channel along the path defined by the guide member.

The cannula has anchor means attached thereto for anchoring it to a disc. In preferred embodiments, the cannula has a tubular member with an oval or elliptical cross section and is constructed of extruded plastic. The preferred anchor means are wires slidably mounted on the cannula tubular member.

The trocar is inserted into the cannula and comprises a shaft having a tapered operating end and a tip on the tapered operating end for anchoring the trocar in body tissue. An adjustable collar on the shaft circumferential surface establishes the length that the trocar is inserted into the cannula.

The percutaneous lumbar diskectomy knife comprises a handle, a shaft attached to the end of the handle having a length of approximately 200 mm and a scimitar-shaped blade attached to the shaft opposite the handle end. The blade has a convex cutting edge for cutting the nucleus of a spinal disc.

The rongeur forceps is an improvement of the type having a pair of first and second scissor-like handles, pivotally connected near one end, a first shaft attached to the second handle at the end nearest the handle pivotal connection, a second shaft pivotally connected to the first handle at the end nearest the handle pivotal connection, with the shafts abutting each other and forming a plane. The second shaft reciprocates relative to the first shaft. The forceps has first and second jaws having scoops; the first jaw rigidly attached to the first shaft, and the second jaw pivotally connected to both the first and second shafts for sweeping an arc about the first shaft pivot connection upon actuation of the handles. The jaw pivot connections are positioned so that the second jaw scoop is in abutting relationship with the first jaw scoop. The improvement comprises positioning the second jaw pivot connections so that the second jaw sweeps an arc of approximately 90° upon handle actuation. Another improved forceps attaches the jaws to the shafts in an intersecting relationship with the plane formed by the shafts.

DESCRIPTION OF THE DRAWINGS

FIG. 3 is a front view of the spinal column without nerves and blood vessels showing infiltration of local anesthetic in tissue around the injured disc with with a spinal needle;

FIG. 4 is an enlarged front view of the injured spinal disc showing insertion of a speculum into the patient's body to create a percutaneous channel to the disc;

FIG. 5 is an enlarged front view showing introduction of the trocar and cannula into the channel created by the speculum;

FIG. 9 is a side elevational view of a speculum constructed in accordance with the teachings of the present invention;

FIG. 10 is an end elevational view of the speculum in its closed position;

FIG. 11 is a bottom sectional view of the speculum taken along 11—11 of FIG. 9;

FIG. 12 is a perspective view of a cannula;

FIG. 13 is a sectional view of the cannula taken along 13—13 of FIG. 12;

FIG. 13A is a perspective view of an alternate embodiment of a cannula;

FIG. 14 is a plan view of a trocar;

FIG. 15 is a plan view of the trocar of FIG. 14 having a cannula inserted over it;

FIG. 16 is a side elevational view of a diskectomy knife constructed in accordance with the teachings of the present invention;

FIG. 16A is an enlarged view of an alternate embodiment of a diskectomy blade;

FIG. 17 is a side elevational view of a straight rongeur forceps constructed in accordance with the teachings of the present invention;

FIG. 18 is a side elevational view of a 45° up-angled rongeur forceps;

FIG. 19 is an enlarged perspective view of a Z-head rongeur constructed in accordance with the teachings of the present invention; and FIG. 20 is a simplified diagram showing a nerve stimulator arranged for use with a cannula and a trocar.

DESCRIPTION OF THE PREFERRED EMBODIMENTS

Method for Performing a Percutaneous Lumbar Diskectomy

Figure 1:
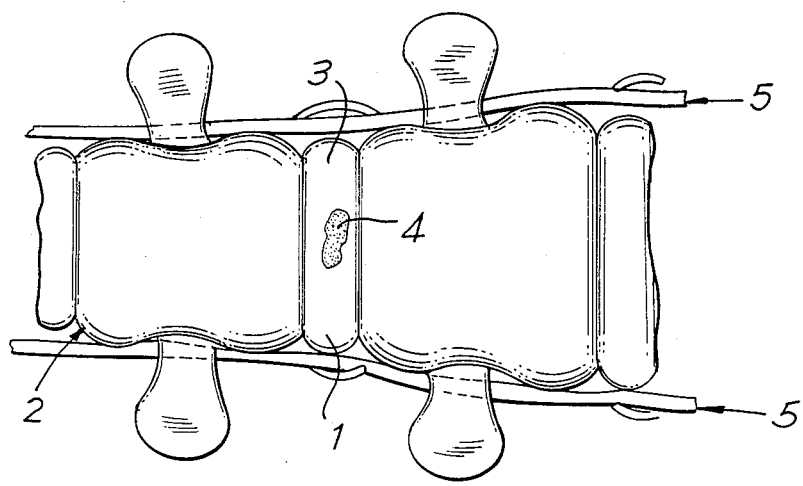
FIG. 1 is an anterior (or front) schematic representation of a disc and two vertebrae also showing the spinal nerves and blood vessels.

Referring to the drawings, FIG. 1 is a schematic view of a lumbar disc shown in its normal position between two vertebrae. This view is a front view. The patient's right side would appear on the lower portion of the drawing and the patient's left side on the upper portion of the drawing. As shown in FIG. 1, spinal nerves run more or less parallel to the spinal column, but some of them branch off in close proximity to the disc capsule.

When the patient suffers from a "slipped disc" the bulging disc stretches the capsule or contacts a nerve that is in close proximity to the disc, and the patient experiences leg pain. Right leg pain means the disc is contacting a nerve on the right side of the spinal column. The converse is true for left leg pain.

In percutaneous lumbar diskectomy procedures, as in laminectomies, a portion of the bulging disc nucleus is removed to alleviate pressure on the spinal nerve. However, if the patient has nerve contact on the left side of the spinal column, the procedure will be performed from the patient's right side, while in a laminectomy or microlaminectomy it would be performed on the left side closer to the bulge. Conversely, if the patient has pain in the right leg, the procedure will be performed from the left side of his body.

In order to remove disc nucleus material, a cannula is passed laterally through the body while the patient is in the lateral decubitus position. Disc removal instruments are passed through the cannula to the disc.

Figure 2:
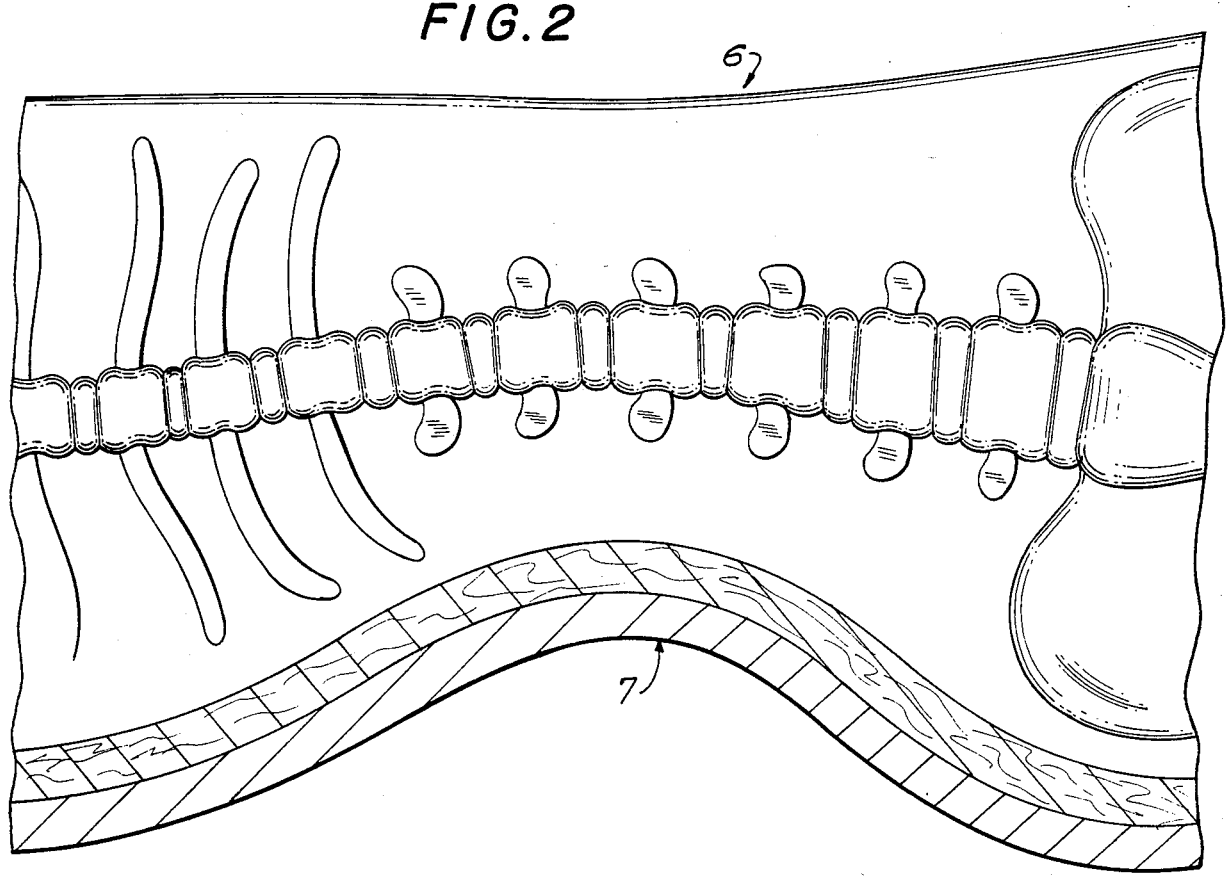
FIG. 2 is a front view of the patient's spinal column without nerves and blood vessels showing proper body positioning prior to the surgical procedure.

To begin the procedure, the patient 6 is placed in the lateral decubitus position on an operating table having a U-shaped convex frame 7 on the table surface, as shown in FIG. 2. When the patient's lumbar spinal region is placed on the frame, his back laterally assumes a curved position that stretches muscles in the area around the injured disc and spreads the vertebrae above and below the disc to allow more maneuvering room for the instruments.

The surgeon may visually monitor the area around the injured disc under fluoroscopic X-ray while percutaneously guiding the instruments. It is recommended that the surgeon wear a lead-lined apron and gloves to reduce his X-ray exposure. The procedure is performed rapidly, within about fifteen minutes, so the patient's total exposure to X-rays is approximately no more than he would experience from a standard X-ray procedure, such as an upper gastrointestinal examination.

The next step in the procedure is to anesthetize the patient with either general or local anesthetic. If the patient is locally anesthetized, the anesthetic is infiltrated around the chosen disc with a long spinal needle. As shown in FIG. 3, the needle 8 is inserted laterally through the patient's side above the pelvic crest and is percutaneously guided to position near the chosen disc under fluoroscopic X-ray. The spinal needle acts as a "go-no-go" indicator. If the needle cannot be properly positioned this indicates that the procedure cannot be used on this particular patient. Normally, the surgeon would then proceed with a standard laminectomy or microsurgical diskectomy.

Infiltration of the anesthetic also spreads the body tissue around the disc, which allows easier insertion of the remaining surgical instruments. Once in place, the needle may act as a guide member or positioning element for instruments that create the percutaneous body channel. Other slender guide members that have diameters less than approximately 3 mm, such as wires, can also be used for positioning elements.

After anesthetization, an approximately one centimeter long skin incision is made above the pelvic crest. As shown in FIG. 4, a percutaneous channel 9 is then created through the incision to the injured disc with a specially designed speculum 10. The speculum 10 is laterally inserted through body tissue in a closed position, i.e., with the blades closed together. The blades have semi-sharp edges which spread rather than cut body tissue. Tissue spreading causes less bleeding and trauma than cutting.

The speculum 10 may have guide means, which is attached to a guide member such as the anesthetization spinal needle. The guide means and fluoroscopic X-ray monitoring insures proper positioning of the speculum near the chosen disc.

Once the speculum is properly positioned, the surgeon spreads its jaw blades thereby creating a channel for cannula insertion. Other channel creating instruments such as a trocar may be used in this procedure; however, a speculum causes the least amount of tissue trauma and bleeding. A trocar can create an acceptable channel, but it creates unnecessary bleeding, hampering the surgeon because blood will tend to flow out of the body through the channel. Similarly, the lateral percutaneous channel may be created by a knife incision, but this will cause even greater bleeding.

Figure 6:
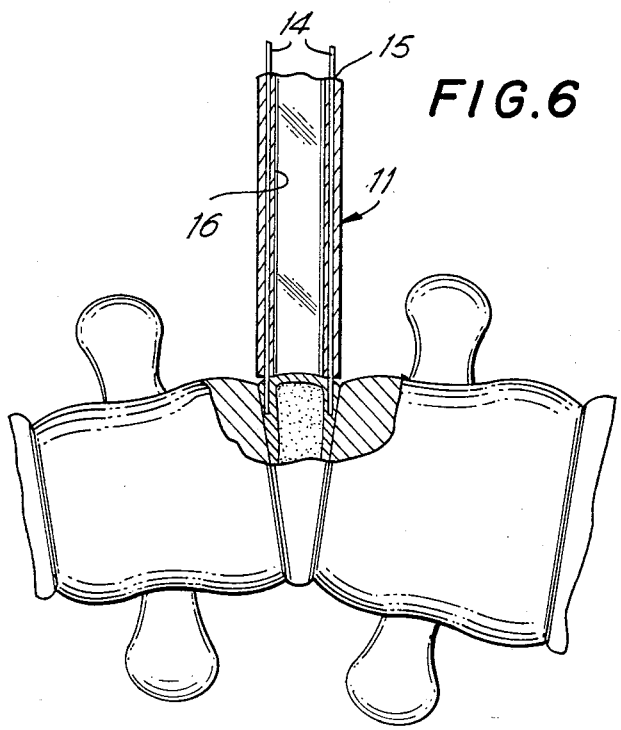
FIG. 6 shows the cannula anchored into the injured disc.

After creation of the body channel, the surgeon introduces a cannula 11 into the channel and then removes the speculum (FIGS. 5 and 6). The cannula acts as a conduit for insertion of surgical instruments through its lumen or bore, and prevents damage to surrounding tissue around the channel which might be caused by the instruments. It should be understood, however, that once inserted, the cannula may act as an instrument conduit for other types of surgical procedures in the spinal column lumbar region such as disc realignment, fusion, or any other surgical or diagnostic procedure.

The cannula 11 may be constructed of metal or of any material compatible with general surgical sterility and mechanical requirements as described herein. It is preferably constructed of flexible, resilient material in order to accommodate minute bends or stresses caused by the surgeon as he manipulates instruments in the cannula.

If the cannula is not flexible, inability to flex it will tend to limit the desired operating area. Cannula flexibility allows it to adjust to slight movements of the surgeon and tends to keep the inserted cannula end next to the chosen operating area on the disc regardless of the movement at the other end on the skin.

It is preferred to use a trocar 12 for insertion of the cannula into the channel created by the speculum. The trocar adds stiffness to the flexible cannula which eases its insertion. It also helps to spread the speculum jaws if they have not opened to the desired channel diameter due to jaw flexibility.

To prevent nerve damage, a nerve stimulator of any conventional type, such as the VARI-STIM III (registered trademark) surgical nerve locator, which is manufactured by Concept, Inc., Clearwater, Fla., may be attached or passed down into the cannula or trocar to indicate if either instrument is hitting one of the spinal nerves or exiting nerve branches. The stimulator will cause motion in one of the patient's legs if it makes nerve contact. If the surgeon sees leg movement, he may back out the cannula and attempt a slightly different insertion position to manipulate around the nerve. FIG. 20 shows a nerve stimulator 80 for use in the procedure. A trocar 12 and a cannula 11 with anchor wires 14 are passed through the skin 82 into a percutaneous channel 9. The nerve stimulator has a ground probe 84 with a needle 85 which is inserted into the skin, and a main probe 86, which transmits an electric current of about 0.5 to 2.0 ma for nerve detection. The probe 86 is applied to the anchor wires 14 and/or the trocar 12, to determine whether the working ends of these instruments are in the vicinity of any nerves. If desired, a nerve stimulator could be used whose main probe is long enough to extend down the cannula to the working ends of the other instruments, or the main probe could be extended by means of a separate wire.

Preferably, the trocar has a pointed tip 13 which is stuck into the disc capsule. By sticking the trocar tip into the disc capsule 3, lateral movement is prevented on the inside end of the cannula relative to the disc, enabling the surgeon to maintain stable continuous contact with the disc 1 during initial cannula 11 positioning. The trocar 12 is guided under fluoroscopic X-ray monitoring.

After the trocar tip pierces the disc, the surgeon removes the speculum 10 by pulling it out. The cannula 11 is anchored into the disc after speculum removal to prevent minute lateral shearing movement of the cannula tip away from this capsule caused by either the patient's or the surgeon's movement.

FIG. 6 shows the cannula 11 anchored into a disc with anchor means. As shown, the anchor means is one or more pieces of wire 14 which are advanced into the disc capsule so that they will prevent relative shearing movement between the cannula and the disc. Slightly curving the wire tips before disc anchoring helps to prevent them from spontaneously pulling out of the disc, yet they are easily removable at the end of the procedure by pulling them out. The anchor wires are preferably slid into apertures 15 within the cannula for ease of manipulation.

The anchor means may also be a jig and support arm assembly permanently mounted on the operating table which positions the cannula and prevents its movement relative to the back disc. However, direct anchoring into the disc is quick, and less expensive than a jig assembly.

Now that the cannula is positioned and anchored into the back disc, the surgeon may perform the diskectomy procedure or any other surgical procedure on the disc that requires access to a disc or spinal column by passing instruments through the cannula lumen 16.

Figure 7:
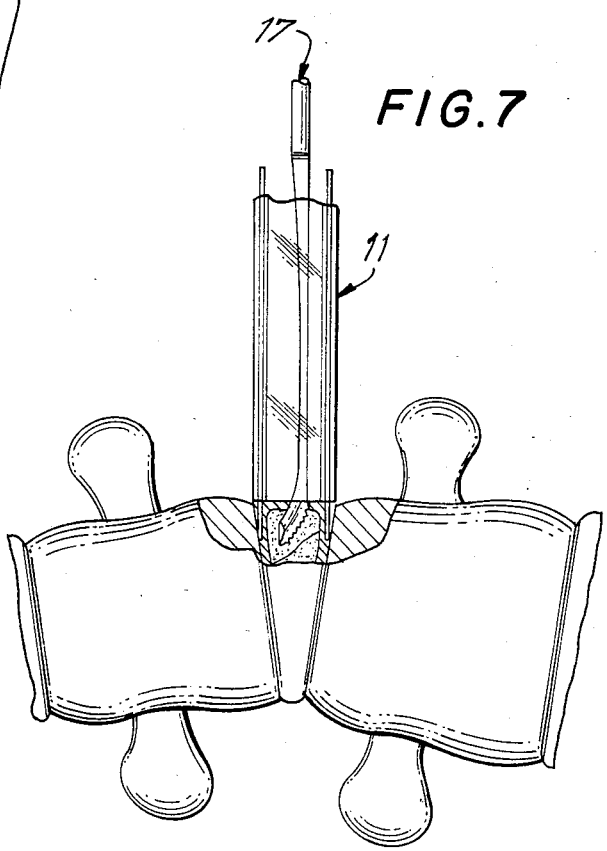
FIG. 7 shows cutting of the disc capsule and nucleus.

As shown in FIG. 7, a knife 17 is inserted into the cannula 11 to cut a hole in the disc capsule, which allows access to the nucleus material. Instead of using a knife, the trocar can have a rotatable reamer built into its tip to cut a hole into the disc capsule.

Once the hole is cut, the knife is inserted through the capsule in order to fragment the nucleus cartilage-like material. Any shape of knife presently used in known diskectomy treatments may be used, but the scimitar-shaped blade shown in FIGS. 16 and 16a is much more efficient for nucleus fragmenting. While the knife is the simplest and probably the most inexpensive way to chop up the nucleus material, other chopping means may be employed, such as ultrasonics, a laser or dissolving chemicals.

Figure 8:
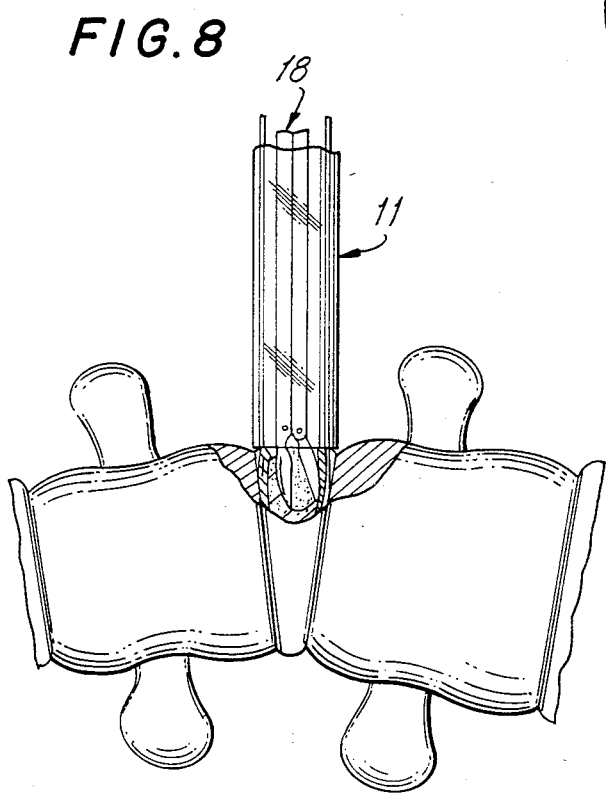
FIG. 8 shows removal of the fragmented nucleus with a rongeur forceps.

Referring to FIG. 8, a rongeur forceps 18, such as those shown in FIGS. 17-19, is inserted down the cannula 11 into the disc to scoop out the fragmented nucleus material. Alternative means to remove material may include other forceps designs or suction. Rongeurs are the preferred instruments for removing chopped nucleus material because they are simple and quick to operate. The rongeur is inserted into the nucleus (under intermittent X-ray visualization) and its jaws or scoops are opened to scoop up a portion of the fragmented material.

When a section of the nucleus is scooped out and removed to form a disc space, the rongeur is reinserted in a new area of the nucleus to scoop out more material. Maneuvering the rongeur into the new area can be difficult because the surgeon has to work through the long cannula. Rongeurs which are constructed in accordance with the teachings of the present invention have larger material grabbing jaws that sweep a wider arc during actuation than known designs. The jaws may also be bent at angles relative to the rongeur shafts.

Rongeurs of the present invention can have large angle jaws because they may pass through the relatively large diameter of the cannula lumen without risk of injury to other tissue structure. The surgeon has the ability to visualize the precise location and movement of the instrument under X-ray visualization.

Jaws that sweep a wide arc are helpful in the present invention procedure because entry to the disc space is from the side opposite the disc bulge. The preferred practice in diskectomies is to remove nucleus material close to the bulge. In the present invention, the surgeon must remove material all the way across the disc in order to get close to the bulge.

A surgeon performing this technique will probably use a series of rongeurs having heads at various angles. Each different head angle will remove nucleus material from different portions of the disc. The first rongeur used should preferably have a straight head as shown in FIG. 17. It tends to smooth the edges of the hole that was cut into the disc capsule as it scoops out a portion of the fragmented nucleus material. The surgeon will then use one or more angle-headed rongeurs to remove other portions of the chopped nucleus. Surgeons familiar with rongeur manipulation will appreciate that the instrument may be rotated about an axis defined by the shafts in order to scoop out material about an axis of revolution.

The relatively large diameter cannula allows use of a rongeur having jaws mounted at an angle intersecting the plane formed by the rongeur shafts. Such jaws are shown in FIG. 19, where they are mounted at roughly a 90° angle relative to the shafts. This is called a "Z-head" rongeur. If the surgeon rotates the Z-head rongeur about the axis formed by the rongeur shaft, he can create a cavity of revolution by removing a large amount of nucleus material.

After emptying the disc space of fragmented nucleus material, it is flushed with saline solution to clean out the space. The solution and any debris contained therein are in turn suctioned out of the space.

The cannula is simply removed after cleaning out the disc space by axially pulling it out of the channel. After removal the surgeon stitches the fat and fascia underneath the skin. The skin is bandaged with an adhesive strip, rather than stitched, to prevent suture scars.

Since the procedure does not damage blood vessels or nerves, post operative pain and complications are minimized. Patient recovery has been found usually to occur within one to two days. Many patients have been able to walk within hours after the operation and outpatient convalesence is contemplated for some patients. The total time necessary to perform this procedure is approximately 15 minutes.

Instruments for Performing a Percutaneous Lumbar Diskectomy

Surgical instruments constructed in accordance with the teachings of the present invention enable the surgeon to quickly and efficiently perform a percutaneous lumbar diskectomy.

FIGS. 9-11 show a speculum 20 used to create the lateral cavity through body tissue into which the cannula will be inserted. The speculum 20 has a pair of semi-sharp edged blades 21 for piercing and stretching body tissue. The semi-sharp edges do not cut tissue, and therefore blood loss is reduced to a minimum. The speculum has a pair of pivotally hinged handles 22 for opening and closing the blades. A lock means allows the surgeon to lock the speculum with the blades in the open position, thus freeing both of his hands. As shown in FIGS. 9 and 10, the lock means is a threaded knob 23 which screws into one handle 22 and contacts the other handle 22. When the knob contacts the other handle the blades cannot close.

The speculum 20 has a guide means for guiding the speculum along a slender member such as a spinal needle 24 or guide wire having a diameter of less than approximately 3 mm, to ensure that the speculum creates a properly positioned channel for disc access. The guide means is any form of bore or series of axially aligned holes defined by the speculum which will slidably receive the the spinal needle. The bore may be incorporated in different embodiments of guide means. Other forms of guide means may be a hole in the front and rear of the blade tip, which allows passage of the spinal needle; a slot on the blade for reception of the spinal needle; or a bore drilled through the blade. In FIGS. 9–11, the guide means is a tube 25 attached to the inside of one of the speculum blades 21. The spinal needle 24 will pass through the tube 25 and guide the speculum 20 into position. The needle 24 passes through a hole 26 in the blade tip.

The preferred embodiment of the cannula 30 is shown in FIGS. 12 and 13. The cannula has a tubular member 31. The member defines a lumen, or hole 32, for passing instruments therethrough from outside the body to inside the body. The member 31 preferably has an oval or elliptical cross section, as shown in FIG. 13, to allow wider instruments to pass through it. For instance, rongeurs having large jaws and angled heads pass through the lumen 32 by aligning their widest part with the major axis of the ellipse. The minor axis is dimensioned to clear the vertebra above and below the disc. The preferred range of cannula diameters are between approximately 8–19 mm.

The cannula may be constructed of metal or of any material compatible with general surgical sterility and mechanical requirements. It is preferably constructed of flexible, resilient material in order to accommodate minute bends or stresses caused by the surgeon as he manipulates instruments in the cannula. It is also preferred that the member material be X-ray transparent so that the entire procedure may be watched under a fluoroscope and the member not obscure the disc area. A suitable X-ray transparent and flexible member material is polyvinyl chloride plastic.

The cannula has anchor means for anchoring it to the disc. As shown in FIG. 12, the anchor means is one or more anchor wires 33 which pierce the the disc capsule and prevent shearing movement between the disc and cannula. In FIG. 13, the anchor wires 33 are slidably inserted into one or more bores 34 defined by the member 31. Slidable wires 33 are preferred because they can be retracted during cannula insertion to prevent their accidental bending or piercing of tissue along the body channel. Alternatively, the anchor wires may be inserted through the lumen and pierced through the disc nucleus.

Sharpened wire ends pierce the capsule easier than unsharpened ends. Once the wire 33 pierces the disc capsule, the outer ends, which are outside the body, may be bent into a U-shape to secure the anchor wires to the member. Alternatively, as shown in FIG. 13A, the anchor wires 33 may also be retained in the axial direction by fastening means, such as a collar 35 containing threaded screws 36. The screws 36 tighten down on the anchor wire to provide an interference fit and lock the anchor wire relative to the cannula. The collar 35 may be part of a handle (not shown) that is attached to the cannula circumference. The handle fastening means may be tab projections around which the anchor wires are bent to retain them. A handle allows the surgeon to generate more controlled leverage as he inserts the cannula into the percutaneous cavity.

Other forms of anchor means may be used for the cannula. For example, sharp tines may be affixed to the cannula tip by constructing them of the member material or by rigidly mounting anchor wires thereto. Alternatively, the cannula tip may be constructed with a screw surface for directly screwing it into body tissue.

An inexpensive cannula may be constructed by extruding the member out of a plastic material such as polyvinyl chloride. Such cannulas may be sold in presterilized packages, along with anchor means such as anchor wires, and discarded after each operation.

FIGS. 14 and 15 show a trocar 40 constructed in accordance with the teachings of the present invention. The trocar has a shaft 41 which is inserted into the cannula 30 as shown in FIG. 15. The cannula 30 abuts against an axially adjustable trocar collar 42 that selectively varies the distance that the trocar is inserted into the cannula. The collar has an annular shape which slides over the shaft. Fastening means such as one or more screws 43 tightens the collar on the shaft.

The shaft has a tapered end 44 for insertion into the body and a tip 45 on the tapered end for anchoring into body tissue. As shown, the shaft 41 may have one or more grooves 46 on its outer surface that run along the axial dimension. The grooves receive protuberances on the lumen such as anchor means.

FIG. 16 shows a percutaneous lumbar diskectomy knife 50 having a handle 51. A shaft 52 is attached to the end of the handle and has a length of approximately 200 mm for insertion into a cannula. A scimitar-shaped blade 53 is attached to the shaft 52 opposite the handle 51. The blade 53 has a convex cutting edge 54 for cutting the capsule and nucleus of the disc. In FIG. 16 the cutting edge is serrated. Alternatively, as shown in FIG. 16A, the blade 55 has a more pronounced curve and the cutting edge 56 is not serrated. The more pronounced curve of blade 55 allows quicker and more efficient fragmentation of disc nucleus material because it tends to undergo a curved cutting path during use.

Referring to the drawings, FIGS. 17–19 show rongeur forceps 60 for removing fragmented disc nucleus material from the disc nucleus space. As shown in FIG. 17, the rongeur has a pair of first 61 and second 62 scissors-like handles which are pivotally connected near one end by pivot 63. Loops 64 and 65 for finger manipulation are on the other end of each handle. A first shaft 66 is attached to the second handle 62 at the end nearest the pivotal connection 63. A second shaft 67 is pivotally connected at a pivot 63a to the first handle 61 at the end nearest pivot 63.

Handle manipulation reciprocates the second shaft 67 relative to the first shaft 66. The shafts are in an abutting relationship such that the first shaft 66 has a first jaw 68 rigidly attached thereto and the second shaft 67 has a second jaw 69 pivotally attached thereto. Each jaw 68 and 69 is attached to the respective shaft end opposite the handle. The jaws 68 and 69 have their open ends in abutting relationship to form a cavity between them. Second jaw 69 has a pivoting hinged connection 70 with first shaft 66 and pivoting connection 71 with second shaft 67 for rotation about the hinge 70 upon actuation of the handles 61 and 62. Spreading the handles 61 and 62 opens the jaw 69 and squeezing the handles closes it.

Rongeurs constructed in accordance with the teachings of the present invention have large jaws for retention of larger amounts of disc material than known rongeurs. The pivoting jaw sweeps a total angle of approximately 90° from the open to the closed position. The 90° sweep allows the rongeur to empty a larger volume of disc space from a given approach position than known rongeurs.

Some of the rongeurs have jaws 68 and 69 mounted at an angle relative to the shafts 66 and 67 such as shown in FIG. 18. Angled jaws allow the surgeon to grab nucleus material in portions of the disc which would not be reachable by rongeurs having a straight head with jaws mounted parallel to the shafts as shown in FIG. 17.

The jaws 68 and 69 may even be attached in an intersecting relationship with the plane formed by the shafts 66 and 67 such as shown in FIG. 19. The jaws perpendicularly intersect the plane established by the two shafts. This is called a Z-head rongeur forceps. With this rongeur design, the surgeon may grab material on each side of the shaft by rotating the rongeurs about the shafts' axial length axis to scoop out a cylinder of rotation in the disc space.

Rongeurs having large jaws and angled heads allow the surgeon to quickly empty the disc space of fragmented material. Large jaws having different angles of attachment relative to the shafts may be used in percutaneous lumbar diskectomies because the cannula has a large lumen which will allow passage of large instruments therethrough. Visualization of the procedure under fluoroscopic X-ray is a safety feature which allows the surgeon to precisely control the rongeur position within the disc space.

All of the above described instruments, or a portion of them may be included in a surgical kit for performance of a percutaneous lumbar diskectomy. The surgeon would then have a complete set of instruments necessary to perform the entire operation, or only a portion of the operation. For instance, a kit might contain a speculum, a cannula, a trocar, one or more diskectomy knives, and one or more rongeurs. If a surgeon elected to insert the cannula with a trocar alone, then he might purchase a kit containing a cannula, trocar, and one or more rongeurs. If a surgeon needs to percutaneously access a disc or other body tissue, he might purchase an apparatus comprising a speculum, a trocar and a cannula. Presterilized disposable cannulas might be sold in addition to the kits. The surgeon would use a fresh cannula for each procedure. Those skilled in the instrument manufacturing arts will appreciate that any combination of the above described instruments may be useful for surgeons. Those kits might also contain known instruments such as curettes and suction tubes.

I claim:

1. A method for percutaneously accessing the lumbar region of a patient's spinal column comprising:
    (a) laterally inserting a cannula through the patient's side above the pelvic crest to contact a predetermined position in the lumbar region; and
    (b) conducting a surgical procedure on the spinal column by manipulating instruments through said cannula.

2. A method for performing a percutaneous lumbar diskectomy comprising:
    (a) laterally inserting a cannula through the patient's side above the pelvic crest to contact a chosen vertebral disc in the lumbar region;
    (b) anchoring the cannula to the disc;
    (c) cutting the disc capsule and nucleus through the cannula in the lumbar region;
    (d) removing a desired amount of disc material through the cannula; and
    (e) removing the cannula.

3. A method for performing a percutaneous lumbar diskectomy comprising:
    (a) positioning the patient in a lateral decubitus position;
    (b) anesthetizing the patient;
    (c) laterally inserting a cannula through the patient's side above the pelvic crest to contact a chosen vertebral disc in the lumbar region;
    (d) anchoring the cannula to the disc;
    (e) cutting the disc capsule and nucleus through the cannula;
    (f) removing a desired amount of disc nucleus through the cannula;
    (g) irrigating the disc nucleus with fluid to clean it;
    (h) suctioning out the fluid; and
    (i) removing the cannula.

4. The method according to any one of claims 1, 2, or 3 comprising:
    (a) viewing the method under fluoroscopic X-ray.

5. The method according to any one of claims 1, 2 or 3 comprising:
    (a) detecting contact with spinal nerves during cannula insertion to prevent nerve damage.

6. The method according to any one of claims 1, 2, or 3, said cannula insertion comprising:
    (a) sliding the cannula over a trocar; and
    (b) laterally inserting the combined cannula and trocar through the patient's side above the pelvic crest to contact a predetermined position in the lumbar region.

7. The method according to any one of claims 1, 2, or 3 wherein:
    (a) said cannula has an outer diameter between approximately eight and nineteen millimeters (8–19 mm).

8. The method according to any one of claims 1, 2, or 3, said cannula insertion comprising:
    (a) laterally inserting a closed speculum through the patient's side above the pelvic crest to a position near the predetermined position in the lumbar region;
    (b) opening the speculum to displace body tissue, thereby creating a channel; and
    (c) inserting the cannula into the channel.

9. The method according to claim 8 comprising:
    (a) sliding the cannula over a trocar; and
    (b) inserting the cannula into said channel with the trocar.

10. The method according to any one of claims 1, 2, or 3 comprising:
    (a) laterally inserting a guide member having a diameter of less than approximately three millimeters through the patient's side above the pelvic crest to a predetermined position in the lumbar region before cannula insertion; and
    (b) guiding cannula insertion with said guide member.

11. The method according to claim 10 wherein
    (a) said guide member is a spinal needle.

12. The method according to claim 11 comprising
    (a) anesthetizing the patient by infiltrating anesthetic in body tissue around the predetermined position in the lumbar region with the spinal needle.

13. A cannula for performing a percutaneous lumbar diskectomy comprising:
    (a) a tubular member having a lumen; and anchor means projecting generally longitudinally from at least one end of the member for anchoring the cannula in spinal disc tissue, thereby preventing shearing movement between the member and the tissue, wherein:

(b) the member has removable fastening means for retaining the anchor means, and defines longitudinal apertures for reception of the anchor means.

14. A cannula comprising:
(a) a tubular member having a lumen;
(b) anchor means attached to at least one end of the member for anchoring the cannula in tissue, thereby preventing shearing movement between the member and the tissue;
(c) removable fastening means on the member for retaining the anchor means; and
(d) apertures defined in the member for reception of the anchor means; wherein
the anchor means is at least one anchor wire extending axially from said at least one end of the member, said anchor wire being slidably inserted into the apertures and attached to the cannula by the fastening means.

15. The cannula according to claim 14, wherein:
(a) the member is constructed of resilient plastic material.

16. The cannula according to claim 15 wherein:
(a) the plastic is polyvinyl chloride.

17. The cannula according to claim 15 wherein:
(a) the member is a one piece extrusion.

18. The cannula according to claim 17 wherein:
(a) the anchor means is molded in place during extrusion.

19. The cannula according to claim 15 wherein:
the member has an outer diameter of between approximately eight and nineteen millimeters (8–19 mm) and a length of approximately one-hundred-forty millimeters (140 mm).

20. The cannula according to claim 14,
(a) the member is constructed of X-ray transparent material.

21. The cannula according to claim 14 wherein:
(a) a nerve stimulator is attached to the member for sensing nerve contact with the cannula, to prevent nerve damage which might be caused by the contact.

22. An improved speculum of the type having pivotally connected handles and semi-sharp blades, the blades having inner surfaces that face each other in opposed relationship, wherein the improvement comprises:
(a) guide means on at least one of the blades for percutaneously guiding the speculum through body tissue on a slender member, the guide member having a diameter of less than approximately three millimeters (3 mm), said guide means having a bore defined by the blade and extending approximately parallel to the blade's longest dimension for slidable reception of the guide member, such that the speculum slides along the guide member and creates a channel along the path defined by the guide member.

23. The improvement according to claim 22 wherein:
(a) the bore is defined by the inner diameter of a tube, said tube being attached to a blade.

24. The improvement according to claim 22 wherein the bore is drilled through the blade.

25. The improvement according to claim 22 wherein the bore is defined by axially aligned holes in the blade.

26. The improved speculum according to claim 22 or claim 23, wherein the improvement comprises:
(a) defining the bore on the blade's inner surface.

27. A trocar for performing a percutaneous lumbar diskectomy comprising:
(a) a shaft having a tapered operating end for percutaneous insertion into the body, a held end, and an outer circumferential surface for slidable insertion of the operating end into a cannula; and
(b) one or more slots extending axially along the outer circumferential surface for reception of protuberances on the inner surface of a cannula lumen, wherein:
(a) the tapered operating end has a tip for anchoring the trocar in spinal disc tissues; and
(b) the shaft has an adjustable collar for establishing the length that the trocar is inserted into a cannula.

28. The trocar according to claim 27 wherein:
(a) the shaft has two grooves spaced one hundred-eighty degrees (180°) apart; and
(b) the collar is annularly shaped and slidably engages the shaft outer circumferential surface, said collar having a threaded fastener for selectively tightening and loosening the collar.

29. The trocar according to claim 28 further comprising:
(a) a nerve stimulator attached to the trocar for sensing nerve contact with the trocar, to prevent nerve damage which might be caused by the contact.

30. An apparatus for percutaneously accessing a patient's internal body tissue comprising:
(a) a speculum having blades for creating a percutaneous body channel; and
(b) a cannula for insertion into the percutaneous body channel between the speculum blades, the cannula having:
(i) a tubular member having a lumen for passage of medical instruments therethrough, and
(ii) anchor means for anchoring the cannula in tissue, thereby preventing shearing movement between the member and the tissue.

31. An apparatus for percutaneously accessing a patient's internal body tissue comprising:
(a) a speculum having blades for creating a percutaneous body channel;
(b) a cannula for insertion into the percutaneous body channel between the speculum blades, the cannula having:
(i) a tubular member having a lumen for passage of medical instruments therethrough, and
(ii) anchor means for anchoring the cannula in tissue, thereby preventing shearing movement between the member and the tissue; and
(c) a trocar for insertion of the cannula between the speculum blades, the trocar being slidably inserted into the cannula, the trocar having:
(i) a shaft having a tapered operating end for insertion into the percutaneous channel, and
(ii) a tip on the tapered operating end for anchoring the trocar in body tissue.

32. An apparatus for percutaneously accessing a patient's internal body tissue comprising:
(a) a speculum having blades for creating a percutaneous body channel;
(b) a cannula for insertion into the percutaneous body channel between the speculum blades, the cannula having:

(i) a tubular member having a lumen for passage of medical instruments therethrough, and
(ii) anchor means for anchoring the cannula in tissue, thereby preventing shearing movement between the member and the tissue; and (c) a trocar for insertion of the cannula between the speculum blades, the trocar being slidably inserted into the cannula, the trocar having:
(i) a shaft having a tapered operating end for insertion into the percutaneous channel; and
(ii) a tip on the tapered operating end for anchoring the trocar in body tissue; wherein:

(d) the cannula member has an oval cross section and aperatures for reception of the anchor means;
(e) the cannula anchor means is one or more anchor wires for slidable insertion into the member aperatures; and
(f) the trocar has an adjustable collar for establishing the length that the trocar is slidably inserted into the cannula.

* * * * *